US007271308B2

(12) United States Patent
Zhang

(10) Patent No.: US 7,271,308 B2
(45) Date of Patent: Sep. 18, 2007

(54) PROCESS FOR ISOMERIZATION OF ALPHA OLEFINS TO INTERNAL OLEFINS

(75) Inventor: Jian Jian Zhang, Wilmington, DE (US)

(73) Assignee: Hercules Incorporated, Wilmington, DE (US)

( * ) Notice: Subject to any disclaimer, the term of this patent is extended or adjusted under 35 U.S.C. 154(b) by 574 days.

(21) Appl. No.: 10/968,608

(22) Filed: Oct. 19, 2004

(65) Prior Publication Data

US 2006/0084831 A1 Apr. 20, 2006

(51) Int. Cl.
*C07C 5/23* (2006.01)
*C07C 5/25* (2006.01)

(52) U.S. Cl. ...................... 585/670; 585/664; 585/665; 585/669

(58) Field of Classification Search ................ 585/664, 585/665, 669, 670
See application file for complete search history.

(56) References Cited

U.S. PATENT DOCUMENTS

| | | | |
|---|---|---|---|
| 3,439,054 | A | 4/1969 | Kroll |
| 3,641,184 | A | 2/1972 | Smith et al. |
| 4,587,374 | A | 5/1986 | Peter |
| 4,777,314 | A | 10/1988 | Provin et al. |
| 4,980,331 | A | 12/1990 | Hoxmeier et al. |
| 5,030,606 | A | 7/1991 | Klabunde |
| 5,252,754 | A | 10/1993 | Bottorff |
| 5,502,018 | A | 3/1996 | Chauvin et al. |
| 5,545,792 | A | 8/1996 | Cox |
| 5,723,712 | A | 3/1998 | Chauvin et al. |
| 5,789,645 | A | 8/1998 | Cox |
| 6,348,132 | B1 | 2/2002 | Zhang |
| 6,355,855 | B1 | 3/2002 | Nguyen et al. |

FOREIGN PATENT DOCUMENTS

| | | |
|---|---|---|
| WO | 0 042 537 | 10/1981 |

OTHER PUBLICATIONS

J. C.S. Chem. Comm, (1973); p. 177, "Vinyl Cations in Acid-catalysed Isomerisations of Acetylenes and Allenes", Barry et al.
J. Am. Chem. Soc. Chem. vol. 86, pp. 5416-5420 (1964); "Iodine-Catalyzed Isomerization of Olefins I. ThermodynamidData from Equilibrium Studies of Positional and GeometricalIsomerizationof 1-Butene and 2-Butene," Golden.
Journal of the American Chemical. Society, 88, pp. 2272-2282 (1966); "Olefin Coordination Compounds of Rhodium III. The Mechanism of Olefin Isomerization", Cramer.
Journal of the American Chemical Society, 95, pp. 2248-2251 (1973., "Iron Carbonyl Catalyzed Isomerization of 3-Ethyl-a-pentene. Multiple Olefin Isomerizations via a π Alyl Metal Hydride Intermediate", Casey et al.
Journal of the American Chemical Society, 87, p. 4017 (1965) "The Tripropynylcarbonium Ion. Charge Delocalization in Ethynyl- and Propynylcarbonium Ions", Richey et al.

*Primary Examiner*—Glenn Caldarola
*Assistant Examiner*—In Suk Bullock
(74) *Attorney, Agent, or Firm*—Joanne Rossi; Gary A. Samuels

(57) ABSTRACT

The present invention relates to embodiments for a process for the isomerization of at least one alpha olefin to an internal olefin via a multi-step process resulting in a mixture comprising alkene isomers and a low level of oligomers. According to the present invention an alkylaluminum compound is used in combination with the Group VIII transition metal salt for interaction with the latter, and thereby generating catalytically active species for the isomerization of 1-alkenes to internal alkenes, wherein this mixture is subsequently combined with an acid washed clay.

75 Claims, No Drawings

PROCESS FOR ISOMERIZATION OF ALPHA OLEFINS TO INTERNAL OLEFINS

TECHNICAL FIELD AND INDUSTRIAL APPLICABILITY OF INVENTION

The present invention relates to embodiments of a process for the isomerization of alpha olefins to internal olefins. More particularly, the present invention relates to a multi-step process resulting in a final mixture comprising alkene isomers and a low level of oligomers.

BACKGROUND OF THE INVENTION

In the paper industry, several processes are known for the isomerization of 1-alkenes (alpha olefins) to result in internal olefins having a variety of uses. For example, internal olefins may be used in the preparation of alkyl succinyl anhydride (ASA), a paper size, by reacting them with maleic anhydride. Alkenes having more than four carbon atoms can be subjected to random isomerization using acids as catalysts (e.g. as described in *J. Chem. Soc. Chem. Commun.* 177 (1973), Barry et al.). However, isomerization processes utilizing acid catalysts are typically accompanied by oligomerization as a side reaction. These oligomers, which do not form adducts with maleic anhydride, lower the effectiveness of the ASA size. Moreover, oligomers may also contribute to the formation of deposits in the paper mill.

U.S. Pat. No. 6,355,855 (Nguyen et al.) generally describes the isomerization of 1-alkenes to internal alkenes in the presence of a catalyst composition comprising (i) salts of Group VIII transition metals and (ii) alkylaluminum compounds. The patent indicates that this combination isomerizes 1-alkenes to internal alkenes with only little formation of oligomers, however, the predominant internal alkene will typically be the 2-alkene, which in most cases will account for at least about 50%, particularly at least about 60%, and the formation of up to 70% or more of the internal alkenes.

U.S. Pat. No. 6,348,132 (Zhang) describes the sizing efficiency of ASA made from a mixture of internal alkenes with a substantially even distribution of isomers.

Thus, it would be desirable to have a process where alpha olefins can be isomerized to internal alkenes, such that the final mixture contains alkene isomers (i.e., 2-alkene, 3-alkene, 4-alkene, etc.) without the simultaneous production of substantial amounts of oligomers such as, for example, olefin dimers.

SUMMARY OF THE INVENTION

The present invention relates to embodiments of a multi-step process for the isomerization of alpha olefin(s) to internal olefin(s), an embodiment of the process comprising:

(a) combining at least one 1-alkene in liquid phase at a temperature of from about 50° C. to about 200° C. with a catalyst, wherein the catalyst is formed by contacting (i) at least one Group VIII transition metal salt and (ii) at least one alkylaluminum compound, thereby resulting in a first mixture; and (b) combining the first mixture of step (a) with at least one acid washed clay, thereby forming a final mixture.

Step (a) of the present invention should be carried out in the substantial absence of water (moisture) and molecular oxygen. To this end it is recommendable to purge the reactor with an inert dry gas (such as, for example, nitrogen or argon) before charging it and to also dry and deoxygenate the starting materials (including alkene, components of the catalytic system and solvent, if used) in any conventional manner before introducing them into the isomerization reactor. Preferably step (a) should be carried out in an inert atmosphere, e.g., under dry nitrogen gas.

Preferably, the at least one Group VIII transition metal includes cobalt and the at least one alkylaluminum compound includes trialkylaluminum compound, wherein when this combination is utilized, the process is carried out in the substantial absence of alkoxyaluminum species.

Generally, the at least one 1-alkene and catalyst in step (a) are combined, and subjected to a temperature of from about 50° C. to about 200° C. wherein the resultant product of step (a) is a first mixture of internal alkenes, where this mixture comprises 1-alkenes in an amount up to about 5 wt-%; 2-alkenes in an amount ranging from about 50 wt-%, particularly at least 60 wt-% and up to about 70 wt-% or more; and less than about 2 wt-% of oligomers.

Step (b) further isomerizes the internal alkenes contained in the first mixture resulting from step (a), thereby producing a final mixture containing more even distribution of alkene isomers and a low level of oligomers.

Step (b) is suitably carried out at a temperature from about 100° C. to about 300° C., preferably at a temperature of from about 120° C. to about 200° C., and more preferably at about 150° C. to about 175° C.

Generally the resultant final mixture of step (b) comprises about 1-5 wt-% of alpha olefins, about 15-50 wt-% of $C_2$ alkenes, about 15-25% of $C_3$ alkenes, about 5-20 wt-% of $C_4$ alkenes, about 10-50 wt-% of $C_5$ and up alkenes and less than about 10 wt-% of dimers, preferably less than about 6 wt-% of dimers.

Other methods or processes, features and advantages of the present invention will be or become apparent to one with skill in the art upon examination of the following detailed description. It is intended that all such additional methods or processes, features and advantages be included within this description and within the scope of the present invention.

DETAILED DESCRIPTION OF A PREFERRED EMBODIMENT OF THE INVENTION

All patents, articles, publications or disclosures described in this application, specifically including U.S. Pat. No. 6,355,855 (Nguyen et al.), are hereby incorporated by reference herein in their entirety.

Where a range of numerical values is recited herein, unless otherwise stated, the range is intended to include the endpoints thereof, and all integers and fractions within the range. It is not intended that the scope of the invention be limited to the specific values recited when defining a range. Moreover, all ranges set forth herein are intended to include not only the particular ranges specifically described, but also any combination of values therein, including the minimum and maximum values recited.

There are several distinct advantages conferred by the embodiments of the present invention including, inter alia, the production of a resultant final mixture comprising alkene isomers as well as a low level of oligomer production (i.e. 10 wt-% or less, preferably 6 wt-% or less).

As used herein and in the appended claims, the terms "combining", "combined", "combination" or other derivations thereof, when used in conjunction with the components of the catalytic composition, it is to be understood that the exact structure of the catalytic species formed upon contact between the components (i) and (ii) is not known. Without wishing to be bound by theory, it is assumed that some kind of reaction (interaction) between these components takes place, which eventually results in the formation of the catalytically active species.

As used herein, the term "substantial absence" means that if alkoxyaluminum species are present, such species are preferably present in only trace amounts, and in any event, in amounts which afford a ratio of alkoxy groups bonded to Al to alkyl groups bonded to Al (in the alkylaluminum compound(s)) that is not higher than 0.1:1, preferably not higher than 0.05:1 and most preferably not higher than 0.01:1. Such low ratios can easily be accomplished by keeping the presence of oxygen (air) during the isomerization at a minimum and excluding the presence of other oxygen-containing species (e.g. anions in the transition metal salt(s)) that might cause oxidation of alkylaluminum compound to alkoxyaluminum species. In order to exclude molecular oxygen it is preferred to purge both the reactor and the starting materials (1-alkene, transition metal salt, solvent etc.) with an inert gas such as nitrogen or argon and to conduct the isomerization in an inert gas atmosphere.

An embodiment of the present invention contemplates a process for the isomerization of alpha olefin(s) (1-alkenes) that ultimately results in a final mixture containing internal alkene(s) and a low level of oligomers, the process comprising:

(a) combining at least one 1-alkene in liquid phase at a temperature of from about 50° C. to about 200° C. with a catalyst, wherein the catalyst is formed by contacting (i) at least one Group VIII transition metal salt and (ii) at least one alkylaluminum compound, thereby resulting in a first mixture; and (b) combining the first mixture of step (a) with at least one acid washed clay, thereby forming a final mixture.

Various embodiments of the process can be carried out batchwise, semicontinuously and continuously. With respect to a semicontinuous process, step (a) could be performed first, wherein the first mixture derived from step (a) could be continuously fed to a tubular reactor for performing step (b). The resident time can be designed so that the desired internal olefin mixture results from step (b) in a continuous manner. An example of a continuous process would be through the use of a two-compartment tubular reactor where the first compartment is packed with the catalyst (i.e. cobalt/TMAL) and the second compartment is packed with calcined acid clay.

The at least one 1-alkene of step (a) generally has at least 4 carbon atoms. Preferably the 1-alkenes will have about 5 to about 40 carbon atoms, more preferably about 6 to about 30 carbon atoms. Although there is no upper limit for the number of carbon atoms from a practical point of view, the number of carbon atoms is primarily determined by the intended use of the desired internal alkenes. Alkenes of about 10 to about 20 carbon atoms (e.g., 16-20 carbon atoms) are particularly desirable substrates if the resulting internal alkenes are to be used for the production of ASA.

The 1-alkene to be isomerized by the process of the present invention may be linear or branched and may also contain a cycloaliphatic or aromatic ring structure. Specific, but non-limiting, examples of suitable 1-alkenes for use in the present invention include at least one of 1-pentene, 3-methyl-1-butene, 2-methyl-1-pentene, 4-methyl-1-pentene, 1-hexene, 1-heptene, 1-octene, 2-methyl-1-octene, 2-ethyl-1-hexene, 5-methyl-1-heptene, 1-nonene, 1-decene, 1-undecene, 1-dodecene, 2-methyl-1-dodecene, 1-tetradecene, 2-methyl-1-tetradecene, 1-hexadecene, 2-methyl-1-hexadecene, 5-methyl-1-hexadecene, 1-octadecene, 2-methyl-1-octadecene, 1-eicosene, 2-methyl-1-eicosene, 1-docosene, 1-tetracosene, 1-hexacosene, vinylcyclohexane and 2-phenyl-1-butene, although the present invention is in no way limited to these examples. Examples of commercially available alpha olefins that may be utilized include, but are not limited to, Neodene® 2024, Neodene® 16, Neodene® 18, and Neodene® 1618 available from Shell Chemical (Geismar, La.); Alpha olefin C16, Alpha olefin C18, and Alpha olefin C16/C18 available from CP Chem (Chevron Phillips chemical Company, Woodland Tex.). The alpha olefin can be single chain length (C16 or C18) or a mixture of different chain lengths. Generally, the alpha olefins (1-alkenes) are used "as is", wherein they are in a liquid phase.

It is, of course, also possible to isomerize more than one type of 1-alkene at the same time. For example, mixtures of two, three, four, five, six and more 1-alkenes can be employed in step (a). Moreover, it is not necessary that the 1-alkenes be employed in a substantially pure or purified form. Rather, they can be employed as a mixture (or contaminated) with one or more other compounds which are not 1-alkenes, provided said other compounds do not substantially interfere with the isomerization. Typical examples of other compounds which may (and often will) be present in the starting material are internal alkenes as well as saturated (cyclo)aliphatic and aromatic hydrocarbons.

The embodiments of the process of the present invention can be carried out both in the presence and absence of solvent. Generally, the presence of solvents are a result of the introduction of the catalyst to the process, wherein the catalyst is typically carried in a solvent, such as for example toluene, however, preferably no further amount of solvent is purposefully added to the process.

While it will usually be preferred to use no additional solvent other than that provided with the catalyst, it may in some situations be advisable or even necessary to work in the presence of additional solvent. For example, if the amount of liquid (and particularly alkene) present is not sufficient to accommodate (dissolve or at least disperse) the (solid or liquid) components of the catalytic system and to afford a not too viscous liquid phase, a solvent or solvent mixture may have to be added. The solvent should have a boiling point that is above the temperature under which the isomerization is to be carried out. Also, if at the end of the process the isomerized alkene is to be separated from the solvent by distillation, care should be taken that the boiling point difference between solvent and alkene is sufficiently large to not unnecessarily complicate said distillation. The solvent should also be miscible with at least the 1-alkene and should not interfere with the isomerization process, particularly not react with any of the other species present. Especially in view of the presence of alkylaluminum compound, the solvent should, of course, not include any active hydrogen atoms that can react with components of the catalytic system (e.g., alkylaluminum compound).

Examples of suitable solvents for use in the present invention are non-polar solvents such as optionally halogenated (particularly chlorinated), aliphatic, cycloaliphatic and aromatic hydrocarbons and aliphatic ethers. These solvents suitably have a boiling point between about 80° C. and about 200° C., particularly about 100° C. and 150° C. Specific examples thereof are toluene, the xylenes, chlorobenzene, dichlorobenzenes, chloroform, carbon tetrachloride, octane, decane, and dodecane as well as mixtures of two or more of these solvents.

According to step (a), at least one Group VIII transition metal salt is used in combination with at least one alkylaluminum compound for interaction with the latter, thereby generating catalytically active species for the isomerization of 1-alkenes to internal alkenes.

While the components of the isomerization catalyst can be combined in any manner which allows interaction thereof with formation of the catalytically active species, a particularly convenient and, thus preferred way is the generation of the catalyst in situ, i.e., inside the isomerization medium. This can simply be accomplished by adding the components of the catalytic system separately to the isomerization reactor. The order and form of addition of the alkene, catalyst components, solvent etc. to the reactor is, however, not critical for the successful operation of the process of the present invention. Moreover, additional reagents and components for the isomerization reaction beyond those set forth above are not necessary and should thus preferably not be present.

Suitable Group VIII transition metal(s) for use in the at least one metal salt of step (a) includes, but is not limited to, at least one of nickel, cobalt, iron, palladium, rhodium, platinum, ruthenium, osmium or iridium, more preferably nickel, cobalt, and palladium. Particularly in view of the activity of the resulting catalytic species, the most preferred Group VIII transition metals are cobalt and palladium, particularly cobalt. Two or more of these metals can be employed in combination, for example, in the form of two or more different transition metal salts.

The anions or ligands of the at least one Group VIII transition metal salt are not particularly limited. Said anions (ligands) can be both inorganic and organic. Examples thereof include halides (e.g., fluorides, chlorides, bromides and iodides), sulfate, nitrate, phosphate, carbonate, carboxylates such as formate, acetate, propionate, oxalate, benzoate, phthalate and naphthoate, chelating agents like acetylacetonate and EDTA, as well as cycloalkadienyl ligands like 1,5-cyclooctadienyl and pentadienyl (metallocenes) etc. Of course, two or more different anions (ligands) may be present, both in the form of a single metal salt and in the form of mixtures of salts (optionally of different metals). Particularly desirable anions (ligands) for the purposes of the present invention are the halides, particularly chloride and bromide and especially chloride, and acetylacetonate.

A suitable Group VIII transition metal salt contains a halogen, particularly chlorine; and/or a chelate-forming ligand, such as acetylacetonate. Other specific examples of corresponding salts include Ni(II) chloride, Ni(II) acetylacetonate, Co(III) acetylacetonate, $PdCl_2$, $PtCl_2$ (cyclooctadienyl)$_2$, Ir(III) acetylacetonate and Rh(III) acetylacetonate. Those skilled in the art will recognize that there are many more other salts that can also be used. Examples of preferred salts include, Ni(II) chloride, Ni(II) acetylacetonate, Rh(III) acetylacetonate; Ir(III) acetylacetonate and Co(III) acetylacetonate; more preferred salts include Ni(II) acetylacetonate, Ir(II) acetylacetonate and Co(III) acetylacetonate. The most preferred Group VII transition metal salt is cobalt (III) acetylacetonate.

The at least one alkylaluminum compound for use in step (a) is not particularly limited, as long as it contains at least one alkyl group directly bonded to an aluminum atom. However, a particularly suitable class of alkylaluminum compounds is that of the general formula: $AlR_aX_b$, in which R represents an alkyl radical, X represents a halogen radical, a is an integer from 1 to 3, b is 0, 1 or 2, and the sum (a+b) is 3.

In the above general formula the alkyl group(s), R, can have any number of carbon atoms, although a range of 1 to about 40 carbon atoms per alkyl group is preferred. Thus, if "a" in the above formula is 3, the corresponding alkylaluminum compound preferably contains a total of not more than about 120, more preferably not more than about 100 carbon atoms. A relatively high total number of carbon atoms may be preferred in cases where the volatility of the alkylaluminum compound should be kept as low possible (e.g., if the isomerization is to be conducted with a relatively high-boiling alkene at a relatively high temperature and under atmospheric pressure). Alkyl groups with a high number of carbon atoms (as determined via the boiling point and melting point of the alkane group in the alkylaluminum compound) may also be of advantage if at the end of the isomerization the catalyst is to be deactivated (destroyed) by the addition of water, resulting, i.e., in the hydrolytic cleavage of the alkyl-Al bond and the generation of the corresponding alkane. If said alkane has a substantially higher boiling point than the alkene(s) present in the reaction medium the separation of the latter from the former by, e.g., distillation is facilitated. Typically, however, the alkyl group(s) of the at least one alkylaluminum compound will have from 1 to about 10, and particularly from 1 to about 6 carbon atoms. An upper limit of 6 carbon atoms may be particularly desirable in cases where the alkenes are relatively high-boiling and the catalyst is to be deactivated by addition of water. This addition of water would then result in the liberation of a relatively low-boiling hydrocarbon (e.g. methane, ethane, hexane etc.) from the alkylaluminum compound which, in turn, would facilitate separation or removal thereof by distillation.

The alkyl groups, R, for use in the alkylaluminum compound(s) can be linear or branched and, for $a \geqq 2$, may be identical or different (usually they are identical). Specific examples thereof are methyl, ethyl, propyl, isopropyl, n-butyl, isobutyl, 2-butyl, n-pentyl, n-hexyl, n-heptyl, 2-ethylhexyl, n-octyl, n-nonyl and n-decyl. Preferred groups R for use in the present invention include methyl, ethyl, n-propyl, isopropyl, n-butyl, 2-butyl, isobutyl, n-pentyl and n-hexyl. Most preferred are methyl and ethyl (also in view of price and availability of corresponding compounds).

Preferred values of "a" in the above general formula are 2 and 3, particularly 3. In other words, preferred alkylaluminum compounds are trialkylaluminum compounds such as trimethylaluminum and triethylaluminum, as well as tributylaluminum, triisobutylaluminum, diethylisobutylaluminum, trihexylaluminum, triheptylaluminum, and trioctylaluminum.

If "b" in the above formula is 1 or 2, i.e., one or two halogen radicals X are present, X is preferably selected from Cl and Br and is most preferably Cl. A preferred representative of the class of alkylaluminum halides is diethylaluminumchloride (DEAC). Preferred further examples thereof include ethylaluminumdichloride and isobutylaluminumdichloride.

While preferred alkylaluminum compounds have been set forth above, it is to be understood that the embodiments of the present invention are not limited to the use of those compounds. Examples of the numerous other compounds that can be used as alkylaluminum compound(s) are ethylaluminum sesquichloride and isobutylaluminum sesquichloride. Generally, the most suitable alkylaluminum compound(s) do not contain any atoms other than aluminum, carbon, hydrogen and, optionally, halogen.

Preferably in step (a), the at least one Group VIII transition metal salt includes cobalt and the at least one alkylaluminum compound includes a trialkylaluminum compound, wherein when this combination is utilized, the process is carried out in the substantial absence of alkoxyaluminum species.

Regarding the relative amounts of 1-alkene(s), Group VIII transition metal salt(s) and alkylaluminum compound(s) used in step (a), said amounts can vary over very broad ranges. In practice, however the molar ratio of 1-alkene to Group VIII transition metal will generally be in the range of from about 1:1 to about 10,000:1, more often from about 10:1 to about 5,000:1. A molar ratio of from about 500:1 to about 4,000:1 and particularly from about 700:1 to about 2,000:1 will often be the most desirable for the purposes of the present invention.

The atomic ratio of Group VIII transition metal(s) to Al in the alkylaluminum compound(s) will usually range from about 2:1 to about 1:500, particularly from about 1:1 to about 1:300, with a range from about 1:2 to about 1:100 being most common. A very high excess of Al over Group VIII transition metal does not offer any particular advantages. On the other hand, too little Al relative to transition metal may sometimes have an adverse effect on the activity of the catalytic system. At any rate, the optimum ratios of 1-alkene, Group VIII transition metal and alkylaluminum compound depend to a large extent on the specific compounds to be employed and can readily be determined by the person of ordinary skill in the art by means of routine experimentation.

Step (a) is suitably carried out at a temperature from about 50° C. to about 200° C., preferably at a temperature of from about 80° C. to about 150° C., and more preferably at about 80° C. to about 120° C. The temperature to be employed is mainly determined by such factors as activity of the catalytic system and the desired reaction time and boiling points (and decomposition temperatures) of the species present in the isomerization medium. Apparently the rate of isomerization will increase with increasing temperature. Higher temperatures will, on the other hand also accelerate undesirable side reactions such as catalyst decomposition and oligomerization and polymerization of the alkenes present. It should also be taken into account that too high of a process temperature may make it necessary, due to the boiling points of the components present, to work under superatmospheric pressure which, although possible, generally increases the overall cost of the process. Therefore, it will usually be most desirable to be able to operate at the minimum temperature that still affords an acceptable rate of isomerization.

As previously noted, step (a) embodiments of the present invention can be carried out at superatmospheric pressure. Apparently it is more convenient, and thus preferred, to be able to operate at, or slightly above, atmospheric pressure. However, certain combinations of temperatures necessary for achieving an acceptable rate of isomerization, and boiling points of one or more of the components of the reaction medium, may sometimes make it unavoidable to use higher than atmospheric pressure.

Typical reaction times for step (a) range from about 1 to about 12 hours, preferably from about 2 to about 6 hours and more preferably from about 2 to about 4 hours (for batch, semi-continuous and continuous processes). The reaction time is, of course, determined by such factors as activity of the catalyst, catalyst concentration, process temperature and desired degree of conversion. Regarding the last factor, it is preferable to achieve degrees of isomerization of about 90 to about 100%, more preferably close to about 100%. If there is a low degree of isomerization (i.e. less than about 90 wt-%), there remains a high level of $C_1$ olefins, which will affect the final mixture resulting from step (b) because most oligomers are formed by the oligomerization of a $C_1$ olefin.

Due to the sensitivity (reactivity) of most alkylaluminum compounds towards oxygen and water, step (a) of the present invention should be carried out in the substantial absence of water (moisture) and molecular oxygen. To this end it is recommendable to purge the reactor with an inert dry gas (such as, for example, nitrogen or argon) before charging it and to also dry and deoxygenate the starting materials (including alkene, components of the catalytic system and solvent, if used) in any conventional manner before introducing them into the isomerization reactor. Remaining traces of oxygen and water in the isomerization medium will usually be scavenged by reaction with the alkylaluminum compound. Of course, it is also highly preferred to as much as possible limit the access of molecular oxygen and water (moisture) to the liquid medium during the isomerization process. Therefore, step (a) should be carried out in an inert atmosphere, e.g., under dry nitrogen gas.

At the end of the isomerization of step (a) the alkene may optionally be separated from the remaining components in any conventional manner such as, e.g., by filtration, distillation, extraction and combinations thereof. In some cases it may be desirable to first convert the alkylaluminum compound into a less moisture-sensitive compound, e.g., by careful addition of water to the isomerization medium. Especially with the more expensive transition metals it will also be necessary for economic reasons to recover the metal values and to optionally recycle them to the process.

In a general and representative sense, the resultant product of step (a) is a first mixture comprising internal alkenes, where this mixture comprises 1-alkenes in an amount up to about 5 wt-%; 2-alkenes in an amount ranging from about 50 wt-%, particularly at least 60 wt-% and up to about 70 wt-% or more; and less than about 2 wt-% of oligomers.

Step (b) of the present invention, comprises combining the first mixture of step (a) with at least one acid washed clay to form a final mixture, which isomerizes the internal alkenes contained in the first mixture resulting from step (a), thereby producing a final mixture containing alkene isomers and a low level of oligomers.

The at least one acid washed clay for use in step (b) includes, but is not limited to, calcined acid washed clays, acid activated bentonite, Engelhard's product F13, F22, F24, and F-20X. The at least one acid washed clay should have a residual acidity ranging from about 1.0 to about 0.025 meq/g, preferably from about 0.5 to about 0.1 meq/g, and more preferably from about 0.4 to about 0.2 meq/g. Mixtures of two or more acid washed clays may also be utilized in step (b) so long as the residual acidity of the acid washed clay mixtures remains within the given desired range.

Most acid washed clays contain substantial amounts of water, and thus before it may be used, the acid washed clay needs to be calcined (a process that is well known in the art) in order to remove the water. In addition to providing for the removal of water, this process also activates the clay catalyst. Typically, for example, the calcination process is performed for at least 1 hour under nitrogen sweeping at a temperature of about 110° C. The moisture is removed in the reaction system because it is problematic, for example, in the production of ASA any water present in the reaction system will convert maleic anhydride to maleic acid. Generally in the calcination process, mechanically held water is driven off by heating in the presence of air to oxidize impurities.

Typically, the acid washed clay(s) are utilized in amounts ranging from about 0.25 wt-% to about 3.0 wt-% (based on the total weight of the olefins), preferably from about 0.5 wt-% to about 2.0 wt-%, more preferably from about 0.75 wt-% to about 1.0 wt-%.

Suitable examples of acids that may be utilized to wash/activate the clays include, but are not limited to, any acid catalyst and/or Lewis acid catalyst known within the art, such as, for example, "$HBF_4$" (i.e. HF (hydrofluoric acid)/$BF_3$ (boron trifluoride)); "$HPF_6$" (i.e., HF (hydrofluoric acid)/$PF_5$ (phosphorus pentafluoride)) and $H_2SO_4$ in dry sulpholane (e.g. as described in *J. Chem. Soc. Chem. Commun.* 177 (1973), Barry et al.).

In accordance with step (a), due to the sensitivity (reactivity) of most alkylaluminum compounds towards oxygen and water, step (b) of the present invention should also be carried out in the substantial absence of water (moisture) and molecular oxygen. To this end it is recommendable to purge the reactor with an inert dry gas (such as, for example, nitrogen or argon) before charging it and to also dry and deoxygenate the starting materials (including alkene, components of the catalytic system and solvent, if used) in any conventional manner before introducing them into the isomerization reactor. Remaining traces of oxygen and water in the isomerization medium will usually be scavenged by reaction with the alkylaluminum compound. Of course, it is also highly preferred to as much as possible limit the access of molecular oxygen and water (moisture) to the liquid medium during the isomerization process. Therefore, step (b) should be carried out in an inert atmosphere, e.g., under dry nitrogen gas.

Step (b) is suitably carried out at a temperature from about 100° C. to about 300° C., preferably at a temperature of from about 120° C. to about 200° C., and more preferably at about 150° C. to about 175° C. The temperature to be employed is mainly determined by such factors as activity of the catalytic system and the desired reaction time It is preferably to operate at the minimum temperature that still affords an acceptable rate of isomerization of the first mixture.

Typical reaction times for step (b) range from about 10 minutes to about 6 hours, preferably from about 20 minutes to about 4 hours and more preferably from about 30 minutes to about 2 hours. The reaction time is, of course, determined by such factors as activity of the catalyst, catalyst concentration, process temperature and desired degree of conversion.

At the end of the isomerization of step (b), the alkenes may be separated from the remaining components in any conventional manner such as, e.g., by filtration, distillation, extraction and combinations thereof. As noted above, the use of more expensive transition metals may necessitate the recovery of the metal values to optionally recycle them to the process of the present invention.

In a general and representative sense, the resultant final mixture of step (b) comprises about 1-5 wt-% of alpha olefins, about 15-50 wt-% of $C_2$ alkenes, about 15-25% of $C_3$ alkenes, about 5-20 wt-% of $C_4$ alkenes, about 10-50 wt-% of $C_5$ alkenes and less than about 10 wt-% of dimers. Preferably, the level of dimers is less than about 6 wt-%.

EXAMPLES

The embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the invention to adapt it to various uses and conditions. Thus various modifications of the present invention in addition to those shown and described herein will be apparent to those skilled in the art from the foregoing description. Although the invention has been described with reference to particular means, materials and embodiments, it is to be understood that the invention is not limited to the particulars disclosed, and extends to all equivalents within the scope of the claims.

According to the present invention and in the following examples, the degree of isomerization and double bond positional distribution (DBPD) were analyzed using $^{13}C$-Nuclear Magnetic Resonance.

In the Examples the following materials were employed:

Alkenes

Neodene16®, a mixture of 1-alkenes having 16 carbon atoms, available from Shell Chemicals (Geismar, La.) and used as received.

Neodene® 18, a mixture of 1-alkenes having 18 carbon atoms, available from Shell Chemicals (Geismar, La.) and used as received.

Example 1

Isomerization of Neodene 18 using $Co(AcAc)_3/Al(Me)_3$ as Catalysts (Performed Using Only Step (a))

All glassware was oven dried, assembled while still hot and cooled under a nitrogen atmosphere. The reaction flask was equipped with a condenser, thermocouple, magnetic stirring bar and nitrogen inlet and outlet. Neodene® 18 (631 g, 2.5 mole), and $Co(AcAc)_3/Al(Me)_3$ (0.298 g, 0.832 mmole) were placed in the flask. The mixture was then sparged with nitrogen for 1 hour followed by addition of 2.1 ml (4.2 mmole) trimethylaluminum solution (2M in toluene). The reaction mixture was heated to 120° C. and remained for three hours. An IR spectrum of the reaction mixture was taken every 60 minutes to see if the reaction had reached the desired conversion. After three hours at 120° C., the IR spectrum of the reaction indicated that the isomerization had reached ~90% conversion. The reaction was continued for two hours. Five reaction samples were taken (every hour of the reaction) were submitted for double bond positional distribution (DBPD) analysis by C-13 nuclear magnetic resonance (NMR), the results are shown in Table 1. The reaction was quenched by a calculated amount of n-butylalcohol. The isomerized olefin was recovered as a colorless liquid after removal of toluene and n-butylalcohol, followed by filtration through an acid clay bed. The recovered olefin was submitted for total olefin and dimer analysis by gas chromatogrqphy (GC).

TABLE 1

Isomerization of Alpha olefin using $Co(AcAc)_3$/TMAL (results found in a mixture resulting from only step (a))

| Olefin Isomers | Rxn Time | C-1 Olefin | C-2 Olefin | C-3 Olefin | C-4 Olefin | ≧C-5 Olefins | Dimer* |
|---|---|---|---|---|---|---|---|
| Sample A | 1 hr | 2.8 | 60.7 | 16.5 | 8.2 | 11.8 | 1.34 |
| Sample A | 2 hrs | 2.3 | 59.1 | 17.2 | 8.7 | 12.7 | 1.32 |
| Sample A | 3 hrs | 2.3 | 59.4 | 17.8 | 8.5 | 12.0 | 1.23 |

TABLE 1-continued

Isomerization of Alpha olefin using $Co(AcAc)_3$/TMAL (results found in a mixture resulting from only step (a))

| Olefin Isomers | Rxn Time | C-1 Olefin | C-2 Olefin | C-3 Olefin | C-4 Olefin | ≧C-5 Olefins | Dimer* |
|---|---|---|---|---|---|---|---|
| Sample A | 4 hrs | 2.4 | 58.6 | 17.9 | 8.8 | 12.3 | 1.31 |
| Sample A | 5 hrs | 2.2 | 58.4 | 18.1 | 8.7 | 12.6 | 1.12 |

*Dimer data was obtained using GC (gas chromatography) analysis. The results in Table 1 are provided as wt-%, based on the total weight of the olefins.

Example 2

Isomerization of Neodene 18 Using an Acid Washed Clay as Catalyst (Performed Using Only Step (b))

The acid washed clay $F_{13}$ (1.0 wt % based on olefin) in the flask was calcined at 110 to 115° C. for 2 hours and kept at ~120° C. under a nitrogen atmosphere. Neodene 16 (50 grams) was added and heated up to 175° C. for 6 hours. Samples were taken every hour to determine DBPD by C-13 NMR, total olefin and dimer by GC (See Table 2). The final olefin was recovered after removal of the clay catalysts by filtration.

TABLE 2

Isomerization of alpha olefin using clay as catalyst (1.0 wt-%) (results found from performing only step (b)).

| Olefin Isomers | Rxn Time | C-1 Olefin | C-2 Olefin | C-3 Olefin | C-4 Olefin | ≧C-5 Olefins | Dimer* |
|---|---|---|---|---|---|---|---|
| Sample B | 1 hr | 2.27 | 34.34 | 22.47 | 17.59 | 23.34 | 10.00 |
| Sample B | 2 hrs | 1.78 | 29.49 | 21.36 | 19.36 | 28.01 | 11.20 |
| Sample B | 3 hrs | 2.06 | 28.40 | 21.46 | 19.03 | 29.05 | 11.80 |
| Sample B | 4 hrs | 1.68 | 26.97 | 21.15 | 20.03 | 30.16 | 11.40 |
| Sample B | 5 hrs | 1.40 | 26.76 | 20.56 | 20.17 | 31.09 | 12.10 |
| Sample B | 6 hrs | 1.18 | 26.37 | 20.53 | 20.53 | 30.58 | 12.20 |

*Dimer data was obtained using GC (gas chromatography) analysis. The results in Table 2 are provided as wt-%, based on the total weight of the olefins.

Example 3

Isomerization of an Alpha Olefin Using Two-Stage Catalytic a Process (Performed Using a Combination of Step (a) and Step (b) According to the Present Invention)

All glassware was oven dried, assembled while still hot and cooled under a nitrogen atmosphere. The reaction flask was equipped with a condenser, thermocouple, magnetic stirring bar and nitrogen inlet and outlet. C-18 alpha olefin (505 g, 2.00 mole), and $Co(AcAc)_3$ (0.2376 g, 0.667 mmole) were placed in the flask. The mixture was then sparged with nitrogen for 1 hour followed by addition of 2.0 ml (4.00 mmole) trimethylaluminum solution (2M in toluene). The reaction mixture was heated to 150° C. and remained for two hours. An IR spectrum of the reaction mixture was taken every 30 minutes to see if the reaction had reached the desired conversion. After two hours at 150° C., the IR spectrum of the reaction indicated that the isomerization had reached ~>95% conversion and also $^1H$ NMR showed only <3% of alpha olefin left. The reaction mixture (Sample C in Table 3, Sample E in Tables 4 & 5) was then transferred to the second flask containing the acid washed clay $F_{13}$ (1.0 wt % based on olefin)—the second stage catalytic process. The clay was calcined at 110 to 115° C. for 2 hours and kept at ~120° C. under a nitrogen blanket. The internal olefin from the first stage was transferred to the clay catalyst. The mixture was then heated up to 150° C.-175° C. for 30 minutes to 4 hours dependent on the clay dosages. The final olefin was filtered to remove all the catalysts while still hot through a silica bed or clay bed ($F_{24}$). The recovered olefin was submitted to determine α-olefin, DBPD by C-13 NMR and total olefin and dimer by GC analysis.

TABLE 3

Isomerization of alpha olefin using $Co(AcAc)_3$/TMAL then clay as catalyst (0.75 wt-%, 175° C.) (results found in final mixture resulting from combination of step (a) and step (b) according to the present invention).

| Olefin Isomers | Rxn Time | C-1 Olefin | C-2 Olefin | C-3 Olefin | C-4 Olefin | ≧C-5 Olefins | Dimer* |
|---|---|---|---|---|---|---|---|
| Sample C | 0 hrs | 2.3 | 59.1 | 17.2 | 8.7 | 12.7 | 1.34 |
| Sample D | 1 hrs | 2.0 | 48.5 | 19.6 | 11.9 | 18.0 | 2.45 |
| Sample D | 2 hrs | 1.8 | 43.1 | 20.3 | 13.6 | 21.2 | 3.44 |
| Sample D | 3 hrs | 1.8 | 38.4 | 20.8 | 15.0 | 23.9 | 3.94 |
| Sample D | 4 hrs | 1.8 | 34.0 | 22.0 | 16.2 | 26.0 | 4.48 |

*Dimer data was obtained using GC (gas chromatography) analysis. The results in Table 3 are provided as wt-%, based on the total weight of the olefins.

TABLE 4

Isomerization of alpha olefin using $Co(AcAc)_3$/TMAL then clay as catalyst (1.0 wt-%, 175° C.) (results found in final mixture resulting from combination of step (a) and step (b) according to the present invention).

| Olefin Isomers | Rxn Time | C-1 Olefin | C-2 Olefin | C-3 Olefin | C-4 Olefin | ≧C-5 Olefins | Dimer* |
|---|---|---|---|---|---|---|---|
| Sample E | 0 hrs | 3.8 | 59.8 | 16.1 | 8.5 | 12.3 | 1.17 |
| Sample F | 0.5 hrs | 2.0 | 24.5 | 20.1 | 19.4 | 33.8 | 5.32 |
| Sample F | 1 hrs | 1.5 | 22.9 | 18.7 | 19.3 | 37.6 | 7.44 |
| Sample F | 1.5 hrs | 1.0 | 19.3 | 16.0 | 19.1 | 44.6 | 8.68 |

*Dimer data was obtained using GC (gas chromatography) analysis. The results in Table 4 is provided as wt-%, based on the total weight of the olefins.

TABLE 5

Isomerization of alpha olefin using $Co(AcAc)_3$/TMAL then clay as catalyst (1.0 wt-%, 150° C.) (results found in final mixture resulting from combination of step (a) and step (b) according to the present invention).

| Olefin Isomers | Rxn Time | C-1 Olefin | C-2 Olefin | C-3 Olefin | C-4 Olefin | ≧C-5 Olefins | Dimer* |
|---|---|---|---|---|---|---|---|
| Sample E | 0 hrs | 3.8 | 59.8 | 16.1 | 8.5 | 12.3 | 1.17 |
| Sample H | 0.5 hrs | 2.6 | 34.8 | 21.1 | 15.1 | 26.4 | 3.60 |

TABLE 5-continued

Isomerization of alpha olefin using $Co(AcAc)_3$/TMAL then clay as catalyst (1.0 wt-%, 150° C.) (results found in final mixture resulting from combination of step (a) and step (b) according to the present invention).

| Olefin Isomers | Rxn Time | C-1 Olefin | C-2 Olefin | C-3 Olefin | C-4 Olefin | ≧C-5 Olefins | Dimer* |
|---|---|---|---|---|---|---|---|
| Sample H | 1 hrs | 1.8 | 26.9 | 19.0 | 18.3 | 35.6 | 4.66 |
| Sample H | 1.5 hrs | 1.0 | 22.9 | 17.4 | 18.1 | 40.6 | 5.64 |

*Dimer data was obtained using GC (gas chromatography) analysis. The results in Table 5 are provided as wt-%, based on the total weight of the olefins.

Example 4

Adduction Reaction of the Isomerized Olefin with Maleic Anhydride to form ASA The laboratory adduction reaction was carried out in a 500 ml 3-necked round bottomed flask. The flask was fitted with a mechanical stirrer, jacketed addition funnel with circulating water (at 75° C.) through it and heating tape (at 85° C.) wrapped around the stop cock of the addition funnel and its connection to the reaction flask. A condenser, heating mantle, nitrogen purge system, thermocouple and temperature controller were also employed. The isomerized olefin (126.27 g, 0.5 mole) was charged to a flask and heated to 196±2° C. with agitation under nitrogen. The molten maleic anhydride (32.66 g, 0.33 mole) mixed with phenolthiazine (0.0057 g) was added slowly to the reactor in period of 2.5 to 3.0 hrs. After the solution had become homogenous, the reaction temperature was raised to 215±2° C., and maintained there for 3 hrs. The unreacted starting material was recovered by vacuum distillation. A light color (6-8, Gardenerscale) residue was collected as the desired product ASA (83.46 g, 94.65% yield based on consumed MA) after the distillation. The recovered ASA was analyzed by GC to determine the residual olefin, ASA assay and the level of dimer.

What is claimed is:

1. A process for the isomerization of 1-alkene to an internal alkene comprising:

a.) combining at least one 1-alkene in liquid phase at a temperature of from about 50° C. to about 200° C. with a catalyst, wherein the catalyst is formed by contacting (i) at least one Group VIII transition metal salt and (ii) at least one alkylaluminum compound thereby resulting in a first mixture; and b.) combining the first mixture of step a) with at least one acid washed clay at a temperature of about 100° C. to about 300° C. to form a final mixture.

2. The process of claim 1, wherein the at least one 1-alkene contains at least 4 carbon atoms.

3. The process of claim 2, wherein the at least one 1-alkene contains about 5 to about 40 carbon atoms.

4. The process of claim 3, wherein the at least one 1-alkene contains about 6 to about 30 carbon atoms.

5. The process of claim 4, wherein the at least one 1-alkene contains about 10 to about 20 carbon atoms.

6. The process of claim 1, wherein the at least one 1-alkene is 1-pentene, 3-methyl-1-butene, 2-methyl-1-pentene, 4-methyl-1-pentene, 1-hexene, 1-heptene, 1-octene, 2-methyl-1-octene, 2-ethyl-1-hexene, 5-methyl-1-heptene, 1-nonene, 1-decene, 1-undecene, 1-dodecene, 2-methyl-1-dodecene, 1-tetradecene, 2-methyl-1-tetradecene, 1-hexadecene, 2-methyl-1-hexadecene, 5-methyl-1-hexadecene, 1-octadecene, 2-methyl-1-octadecene, 1-eicosene, 2-methyl-1-eicosene, 1-docosene, 1-tetracosene, 1-hexacosene, vinylcyclohexane, 2-phenyl-1-butene or mixtures thereof.

7. The process according to claim 1, wherein the at least one Group VIII transition metal is at least one of nickel, cobalt, iron, palladium, rhodium, platinum, ruthenium, osmium, iridium or mixtures thereof.

8. The process according to claim 7, wherein the at least one Group VIII transition metal is at least one of nickel, cobalt, palladium or mixtures thereof.

9. The process according to claim 8, wherein the at least one Group VIII transition metal is at least one of cobalt, palladium or mixtures thereof.

10. The process of claim 1, wherein the at least one Group VIII transition metal salt comprises a halogen.

11. The process of claim 10, wherein the halogen is chlorine.

12. The process of claim 1, wherein the at least one Group VIII transition metal salt comprises a chelate-forming ligand.

13. The process of claim 12, wherein the chelate-forming ligand is acetylacetonate.

14. The process according to claim 1, wherein the at least one Group VIII transition metal salt includes at least one compound selected from Ni(II) chloride, Ni(II) acetylacetonate, Co(III) acetylacetonate, $PdCl_2$, $PtCl_2$ (cyclooctadienyl)$_2$, Ir(III) acetylacetonate or Rh(III) acetylacetonate.

15. The process according to claim 14, wherein the at least one Group VIII transition metal salt includes at least one compound selected from Ni(II) chloride, Ni(II) acetylacetonate, Rh(III) acetylacetonate; Ir(III) acetylacetonate or Co(III) acetylacetonate.

16. The process according to claim 15, wherein the at least one Group VIII transition metal salt includes at least one compound selected from Ni(II) acetylacetonate, Ir(III) acetylacetonate or Co(III) acetylacetonate.

17. The process according to claim 16, wherein the at least one Group VIII transition metal salt is cobalt (III) acetylacetonate.

18. The process according to claim 1, wherein if the at least one Group VIII transition metal salt includes cobalt and the at least one alkylaluminum compound includes a trialkylaluminum compound, the process is carried out having a substantial absence of alkoxyaluminum species.

19. The process according to claim 1, wherein the at least one alkylaluminum compound comprises a compound having the general formula: $AlR_aX_b$, wherein R is an alkyl radical, X is a halogen radical, a is an integer from 1 to 3, b is 0, 1 or 2, and the sum (a+b) is 3.

20. The process of claim 19, wherein the radical R represents alkyl of from 1 to about 40 carbon atoms.

21. The process of claim 20, wherein the radical R represents alkyl of from 1 to about 10 carbon atoms.

22. The process of claim 21, wherein the radical R represents alkyl of from 1 to about 6 carbon atoms.

23. The process of claim 19, wherein the radical R is selected from methyl, ethyl, n-propyl, isopropyl, n-butyl, 2-butyl, isobutyl, n-pentyl, n-hexyl, n-heptyl, 2-ethylhexyl, n-octyl, n-nonyl, and n-decyl.

24. The process of claim 23, wherein the radical R is selected from methyl, ethyl, n-propyl, isopropyl, n-butyl, 2-butyl, isobutyl, n-pentyl, and n-hexyl.

25. The process of claim 19, wherein a is 2 or 3.

26. The process of claim 25, wherein a is 3.

27. The process of claim 19, wherein b is 1 or 2.

28. The process of claim 19, wherein X includes Cl or Br.

29. The process of claim 28, wherein X includes Cl.

30. The process according to claim 19, wherein the at least one alkylaluminum compound is a trialkylaluminum compound or an alkylaluminum halide.

31. The process according to claim 30, wherein the trialkylaluminum compound is trimethylaluminum, triethylaluminum, tributylaluminum, triisobutylaluminum, diethylisobutylaluminum, trihexylaluminum, triheptylaluminum or trioctylaluminum.

32. The process according to claim 30, wherein the alkylaluminum halide is diethylaluminumchloride (DEAC), ethylaluminumdichloride or isobutylaluminumdichloride.

33. The process of claim 1, wherein the 1-alkene and Group VIII transition metal are in a molar ratio of from about 1:1 to about 10,000:1.

34. The process of claim 33, wherein the molar ratio is from about 10:1 to about 5,000:1.

35. The process of claim 34, wherein the molar ratio is from about 500:1 to about 4,000:1.

36. The process of claim 35, wherein the molar ratio is from about 700:1 to about 2,000:1.

37. The process of claim 1, wherein the Group VIII transition metal(s) and Al in the alkylaluminum compound(s) are in an atomic ratio of from about 2:1 to about 1:500.

38. The process of claim 37, wherein the atomic ratio is from about 1:1 to about 1:300.

39. The process of claim 38, wherein the atomic ratio is from about 1:2 to about 1:100.

40. The process according to claim 1, wherein the temperature of step (a) ranges from about 80° C. to about 150° C.

41. The process according to claim 40, wherein the temperature of step (a) ranges from about 80° C. to about 120° C.

42. The process according to claim 1, wherein step (a) has a reaction time ranging from about 1 hour to about 12 hours.

43. The process according to claim 42, wherein step (a) has a reaction time ranging from about 2 hours to about 6 hours.

44. The process according to claim 43, wherein step (a) has a reaction time ranging from about 2 hours to about 4 hours.

45. The process according to claim 1, wherein step (a) results in a degree of isomerization of about 90% or greater.

46. The process according to claim 1, wherein the first mixture comprises up to about 5 wt-% of 1-alkene, about 50 wt-% to about 70 wt-% or more of 2-alkene and less than about 2 wt-% of oligomers.

47. The process according to claim 1, wherein step (b) has a reaction time ranging from about 10 minutes to about 6 hours.

48. The process according to claim 47, wherein the reaction time ranges from about 20 minutes to about 4 hours.

49. The process according to claim 48, wherein the reaction time ranges from about 30 minutes to about 2 hours.

50. The process according to claim 1, wherein the at least one acid washed clay is a calcined acid washed clay.

51. The process according to claim 50, wherein the calcined acid washed clay is an acid activated Bentonite, Engelhard's product $F_{13}$, $F_{22}$, $F_{24}$, $F_{20X}$ or mixtures thereof.

52. The process according to claim 1, wherein the at least one acid washed clay has a residual acidity ranging from about 1.0 to about 0.025 meq/g.

53. The process according to claim 52, wherein the at least one acid washed clay has a residual acidity ranging from about 0.5 to about 0.1 meq/g.

54. The process according to claim 53, wherein the at least one acid washed clay has a residual acidity ranging from about 0.4 to about 0.2 meq/g.

55. The process according to claim 1, wherein the at least one acid washed clay is utilized in amounts ranging from about 0.25 wt-% to about 3.0 wt-% based on olefins.

56. The process according to claim 55, wherein the at least one acid washed clay is utilized in amounts ranging from about 0.5 wt-% to about 2.0 wt-%.

57. The process according to claim 56, wherein the at least one acid washed clay is utilized in amounts ranging from about 0.75 wt-% to about 1.0 wt-%.

58. The process according to claim 1, wherein in step (b) the temperature ranges from about 120° C. to about 200° C.

59. The process according to claim 58, wherein the temperature ranges from about 150° C. to about 175° C.

60. The process according to claim 1, wherein the final mixture of step (b) comprises about 1-5 wt-% of alpha olefins, about 15-50 wt-% of $C_2$ alkenes, about 15-25 wt-% of $C_3$ alkenes, about 5-20 wt-% of $C_4$ alkenes, about 10-50 wt-% of $C_5$ and up alkenes and less than about 10 wt-% of dimers.

61. The process according to claim 60, wherein the final mixture contains less than about 6 wt-% of dimers.

62. The process of claim 1, wherein step (a) is carried out in the presence of solvent.

63. The process of claim 62, wherein the solvent is selected from aliphatic, cycloaliphatic and aromatic hydrocarbons, halogenated aliphatic, cycloaliphatic and aromatic hydrocarbons, aliphatic ethers and mixtures thereof.

64. The process of claim 1, wherein step (a) is carried out in the absence of solvent.

65. The process of claim 1, wherein step (a) is carried out under substantially anhydrous conditions.

66. The process of claim 1, wherein step (a) is carried out in the substantial absence of molecular oxygen.

67. The process of claim 1, wherein the process is carried out batchwise.

68. The process of claim 1, wherein the process is carried out in a semi-continuous fashion.

69. The process of claim 1, wherein the process is carried out in a continuous fashion.

70. The process of claim 1, wherein the catalyst is formed in situ.

71. The process of claim 1, wherein the predominant isomerization product is 2-alkene.

72. The process of claim 1, wherein at least one 1-alkene having from 6 to 30 carbon atoms is contacted, at a temperature from about 80 to about 150° C. and under substantially anhydrous conditions and in the substantial absence of molecular oxygen, with at least one Group VIII transition metal salt selected from chlorides and acetylacetonates of Ni, Co and Pd and with at least one alkylaluminum compound selected from trimethylaluminum, triethylaluminum and diethylaluminumchloride, the 1-alkene(s) and Group VIII transition metal(s) having a molar ratio of from about 100:1 to about 2,000:1, and the Group VIII transition metal(s) and Al in the alkylaluminum compound(s) having an atomic ratio of from about 1:2 to about 1:100, thereby forming internal olefin comprised of at least about 60 mole-% of 2-alkene(s), without concurrent formation of more than about 5% of oligomers.

73. A process for the isomerization of 1-alkene to an internal alkene comprising:

a.) combining at least one 1-alkene in liquid phase and at a temperature of from about 50° C. to about 200° C. with a catalyst, wherein the catalyst is formed by contacting (i) at least one Group VIII transition metal salt and (ii) at least one alkylaluminum compound thereby resulting in a first mixture; wherein the alkylaluminum compound contains at least one alkyl group directly bonded to an aluminum atom and b.) combining the first mixture of step a) with at least one acid washed clay to form a final mixture.

74. A process for the isomerization of 1-alkene to an internal alkene comprising:

a.) combining at least one 1-alkene in liquid phase and at a temperature of from about 50° C. to about 200° C. with a catalyst, wherein the catalyst is formed by contacting (i) at least one Group VIII transition metal salt and (ii) at least one alkylaluminum compound thereby resulting in a first mixture; wherein the alkylaluminum compound contains at least one alkyl group directly bonded to an aluminum atom and wherein if the at least one Group VIII transition metal salt includes cobalt and the at least one alkylaluminum compound includes a trialkylaluminum compound, the process is carried out having a substantial absence of alkoxyaluminum species, and b.) combining the first mixture of step a) with at least one acid washed clay to form a final mixture.

75. A process for the isomerization of 1-alkene to an internal alkene comprising:

a.) combining at least one 1-alkene in liquid phase and at a temperature of from about 50° C. to about 200° C. with a catalyst, wherein the catalyst is formed by contacting (i) at least one salt of a Group VIII transition metal selected from cobalt, iron, palladium, platinum, osmium, iridium, rhodium, ruthenium and mixtures thereof and (ii) at least one alkylaluminum compound thereby resulting in a first mixture; wherein the alkylaluminum compound contains at least one alkyl group directly bonded to an aluminum atom and wherein if the at least one Group VIII transition metal salt includes cobalt and the at least one alkylaluminum compound includes a trialkylaluminum compound, the process is carried out having a substantial absence of alkoxyaluminum species, and b.) combining the first mixture of step a) with at least one acid washed clay to form a final mixture.

* * * * *